United States Patent
Huang et al.

(10) Patent No.: US 10,030,804 B2
(45) Date of Patent: Jul. 24, 2018

(54) INNER DETECTING DEVICE FOR SUBSEA OIL AND GAS PIPELINE

(71) Applicant: Tsinghua University, Beijing (CN)

(72) Inventors: Songling Huang, Beijing (CN); Wei Zhao, Beijing (CN); Shen Wang, Beijing (CN); Xinjie Yu, Beijing (CN); Junjie Chen, Beijing (CN); Zheng Wei, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 381 days.

(21) Appl. No.: 14/759,300

(22) PCT Filed: Sep. 16, 2014

(86) PCT No.: PCT/CN2014/086655
§ 371 (c)(1),
(2) Date: Jul. 6, 2015

(87) PCT Pub. No.: WO2015/074456
PCT Pub. Date: May 28, 2015

(65) Prior Publication Data
US 2015/0346154 A1    Dec. 3, 2015

(30) Foreign Application Priority Data

Nov. 23, 2013    (CN) .......................... 2013 1 0598515
Nov. 23, 2013    (CN) .......................... 2013 1 0598517
Nov. 23, 2013    (CN) .......................... 2013 1 0598590

(51) Int. Cl.
*G01M 3/40*    (2006.01)
*G01N 27/82*    (2006.01)
(Continued)

(52) U.S. Cl.
CPC ............ *F16L 55/38* (2013.01); *G01M 3/40* (2013.01); *F16L 2101/30* (2013.01); *G01N 27/82* (2013.01)

(58) Field of Classification Search
CPC ......... G01N 27/83; G01N 27/82; F16L 11/08; F16L 11/083; F16L 2101/30; F16L 55/38; G01M 3/40
See application file for complete search history.

(56) References Cited

U.S. PATENT DOCUMENTS 5,864,232 A    1/1999    Laursen
6,087,830 A *  7/2000    Brandly ............... G01M 3/005
                                                    324/220
(Continued)

FOREIGN PATENT DOCUMENTS

CN         1942762 A      4/2007
CN       101324477 A     12/2008
(Continued)

*Primary Examiner* — Randy Gibson
*Assistant Examiner* — Gedeon M Kidanu
(74) *Attorney, Agent, or Firm* — Kile Park Reed & Houtteman PLLC (57) ABSTRACT

An inner detecting device for subsea oil and gas pipeline includes a support shaft defining a sealed chamber therein; a packer cup coupled to the support shaft; a hinge assembly coupled to the support shaft, swinging with respect to the support shaft in a radial direction and sliding with respect to the support shaft in an axial direction; a magnetic detector connected to the hinge assembly to move with respect to the support shaft in the radial and axial directions, and the magnetic detector tending to move away from the support shaft in the radial direction; a battery pack; an electric recorder electrically connected to the battery pack; and a mileage recorder recording a travel distance of the inner detecting device within the pipeline.

13 Claims, 5 Drawing Sheets

(51) Int. Cl.
*F16L 11/08* (2006.01)
*F16L 55/38* (2006.01)
F16L 101/30 (2006.01)

(56) References Cited

U.S. PATENT DOCUMENTS

| | | | | |
|---|---|---|---|---|
| 6,847,207 | B1* | 1/2005 | Veach | F16L 55/26 |
| | | | | 324/220 |
| 7,143,659 | B2* | 12/2006 | Stout | F17D 5/00 |
| | | | | 324/71.2 |
| 7,683,611 | B2* | 3/2010 | Burkhardt | G01N 27/82 |
| | | | | 324/220 |
| 7,798,023 | B1* | 9/2010 | Hoyt | F16L 55/28 |
| | | | | 73/865.8 |
| 8,020,460 | B1* | 9/2011 | Hoyt | G01N 27/82 |
| | | | | 324/220 |
| 2012/0038354 | A1* | 2/2012 | Gies | G01N 27/902 |
| | | | | 324/240 |

FOREIGN PATENT DOCUMENTS

| | | |
|---|---|---|
| CN | 103604022 A | 2/2013 |
| CN | 103235034 A | 8/2013 |

* cited by examiner

INNER DETECTING DEVICE FOR SUBSEA OIL AND GAS PIPELINE

CROSS REFERENCE TO RELATED APPLICATIONS

This application claims priority and benefits of Chinese Patent Applications No. 201310598517.0, No. 201310598590.8, No. 201310598515.1, filed with State Intellectual Property Office on Nov. 23, 2013, the entire content of which is incorporated herein by reference.

FIELD

Embodiments of the present invention generally relate to a field of subsea oil and gas transportation, particularly to an inner detecting device for subsea oil and gas pipeline.

BACKGROUND

A safety of subsea oil and gas pipeline is a key technology of the offshore oil and gas exploration technology. Comparing with a land oil and gas pipeline, the subsea oil and gas pipeline is more digamous for environment and has more complicated working condition, so that routine inspecting and maintaining is significant for the safety of subsea oil and gas pipeline.

An inner detecting device for subsea oil and gas pipeline must have a good travel capability within the pipeline which has a complicated structure, for example the pipeline has vertical sections connected to the oil platform, and the bended connector of the oil platform has a turning radius of 1.5 D, so that the deformability of the inner detecting device corresponding to the inner wall of the pipeline is important for the inner detecting device to travel within the pipeline smoothly.

Conventional leakage detecting devices for the oil and gas pipeline generally have fixed magnetized shaft body and odometer wheel system, for example a high definition mechanical system of pipe leakage detectors are described in Chinese Pat. No. 200710118862.4. Due to structures of the fixed magnetized shaft body and odometer wheel system, the conventional leakage detecting device has a poor deformability, in other words, the minimum radial and axial dimensions of the leakage detecting device too large to be adapted to travel within the pipeline which has the vertical sections and less turning radius.

SUMMARY

Embodiments of the present invention seek to solve at least one of the problems existing in the related art to at least some extent.

An inner detecting device for subsea oil and gas pipeline according to embodiments of the present invention includes a support shaft defining a sealed chamber therein; a packer cup coupled to the support shaft along a circumferential direction of the support shaft; a hinge assembly coupled to the support shaft, swinging with respect to the support shaft in a radial direction of the support shaft and sliding with respect to the support shaft in an axial direction of the support shaft; a magnetic detector connected to the hinge assembly to move with respect to the support shaft in the radial and axial directions of the support shaft, and the magnetic detector tending to move away from the support shaft in the radial direction of the support shaft; a battery pack disposed within the sealed chamber; an electric recorder disposed within the sealed chamber and electrically connected to the battery pack; and a mileage recorder disposed on the support shaft to record a travel distance of the inner detecting device within the pipeline.

In some embodiments, the hinge assembly includes a first hinge arm having a first end pivotally and movably coupled to the support shaft and a second end pivotally connected to the magnetic detector; and a second hinge arm having a first end pivotally coupled to the support shaft and a second end pivotally connected to the first hinge arm.

In some embodiments, the hinge assembly further includes a mounting seat fixed to the support shaft and defining a mounting groove therein, the first end of the first hinge arm has a pivot shaft rotatablly and movably fitted into the mounting groove, and the first end of the second hinge arm is pivotally connected to the mounting seat.

In some embodiments, the magnetic detector includes a magnetic conductor; a hinge mount disposed at a front end of the magnetic conductor and pivotally connected to the second end of the first hinge arm via a connecting shaft; a plurality of magnets disposed above the magnetic conductor to form a closed magnetic flux loop; a finger-shaped detector disposed on the magnetic conductor and located in a center of the closed magnetic flux loop; a guide element disposed at rear end of the magnetic conductor and coupled to the support shaft, and the guide element being moved with respect to the support shaft in the radial and axial directions of the support shaft; and a first elastic element disposed between the magnetic conductor and support shaft to normally push the magnetic conductor move away from the support shaft in the radial direction of the support shaft.

In some embodiments, the first elastic element is a spring, the magnetic conductor has a mounting hole and a guide post within the mounting hole, the spring is fitted over the guide post, a first end of the spring is disposed within the mounting hole and a second end of the spring is contacted with the support shaft.

In some embodiments, the support shaft define a guide groove formed in a rear end of the support shaft and extended in the radial direction of the support shaft, the guide element is fitted into the guide groove and is movable in the radial and axial directions of the support shaft within the guide groove.

In some embodiments, one end of the guide groove is extended to an outer surface of the support shaft in the radial direction of the support shaft, and a stop ring is fitted over the outer surface of the support shaft to prevent the guide element getting from moving out of the guide groove in the radial direction of the support shaft.

In some embodiments, a number of the magnetic detector is equal to that of the hinge assembly and is at least 2.

In some embodiments, the mileage recorder includes a pivot seat fixed to the support shaft; a swing arm having a first end pivotally connected to the pivot seat via a pivot shaft and a second end; an odometer wheel connected to the second end of the swing arm to contact with an inner wall of the subsea oil and gas pipeline and defining an axis hole; a rotary encoder disposed in the axis hole of the odometer wheel to record a travel distance of the odometer wheel; and a second elastic element connected between the swing arm and the pivot seat to normally drive the swing arm to rotate away from the support shaft.

In some embodiments, the packer cup comprises front and rear packer cups, and a ratio of a distance between the front and rear packer cups to an inner radius of the pipeline is 1:1 to 1:1.5.

In some embodiments, front and rear mounting flanges are formed at front and rear portions of the support shaft respectively, and the front and rear packer cups are mounted to the front and rear mounting flanges respectively via stainless press plates.

In some embodiments, the magnetic detector further comprises a concentrator disposed below the finger-shaped detector, the rear mounting flange defines a through-hole therein, a plurality of wires of the finger-shaped detector are concentrated to be a wire harness via the concentrator, so that a plug of the wire harness is connected to a socket of the finger-shaped detector through the through hole, the plug and the socket are made of nitrile-butadiene rubber and capable of bearing pressure of 0-20 MPa.

In some embodiments, the battery pack includes a first radial seal disposed between the battery pack and an inner wall of the sealed chamber in the radial direction of the support shaft, a first axial seal disposed between the battery pack and the inner wall of the sealed chamber in the axial direction of the support shaft; and a first damping element disposed on an outer surface of the battery pack and made of polytetrafluoroethylene.

In some embodiments, the electric recorder includes a second radial seal disposed between the electric recorder and an inner wall of the sealed chamber in the radial direction of the support shaft, a second axial seal disposed between the electric recorder and the inner wall of the sealed chamber in the axial direction of the support shaft; and a second damping element disposed on an outer surface of the electric recorder and made of polytetrafluoroethylene.

In some embodiments, the battery pack and the electric recorder are coaxially disposed and a rear end of the battery pack is connected to a front end of the electric recorder Comparing with the conventional inner detecting device with a fixed magnetized shaft body, with the magnetic detector which can move with respect to the support shaft in the radial and axial directions, a travel capability within the pipeline of the inner detecting device of present invention is dramatically increased, and a weight of the inner detecting device can be reduced. Thus, the inner detecting device of present invention is more suitable for the oil and gas pipeline with vertical sections.

Moreover, the inner detecting device of the present invention integrates functions of driving, magnetized detecting, electronic recording, power supplying and mileage recording into one single device, thus maximally decreasing a total length and avoiding a multi-sections type structure of the inner detecting device.

BRIEF DESCRIPTION OF THE DRAWINGS

These and other aspects and advantages of embodiments of the present invention will become apparent and more readily appreciated from the following descriptions made with reference to the accompanying drawings, in which.

DETAILED DESCRIPTION

In order to make the problem to be solved, the technical proposal and the beneficial effects of the present invention move transparent, detailed descriptions of the present invention will be made combined with attached drawings and embodiments. It should be understood that specific embodiments described herein are just used to illustrate the present invention, and not to limit the present invention.

Reference will be made in detail to embodiments of the present disclosure. The same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure.

In the specification, unless specified or limited otherwise, relative terms such as "central", "longitudinal", "lateral", "front", "rear", "right", "left", "inner", "outer", "lower", "upper", "horizontal", "vertical", "above", "below", "up", "top", "bottom", "inner", "outer", "clockwise", "anticlockwise" as well as derivative thereof (e.g., "horizontally", "downwardly", "upwardly", etc.) should be construed to refer to the orientation as then described or as shown in the drawings under discussion. These relative terms are for convenience of description and do not require that the present disclosure be constructed or operated in a particular orientation. In addition, terms such as "first" and "second" are used herein for purposes of description and are not intended to indicate or imply relative importance or significance.

In the description of the present disclosure, unless specified or limited otherwise, it should be noted that, terms "mounted," "connected" "coupled" and "fastened" may be understood broadly, such as permanent connection or detachable connection, electronic connection or mechanical connection, direct connection or indirect connection via intermediary, inner communication or interreaction between two elements. These having ordinary skills in the art should understand the specific meanings in the present disclosure according to specific situations.

The present invention will be further described with reference to the drawings and embodiments, an inner detecting device for 18 inches (457.2 mm) subsea oil and gas pipeline will be an example to be described.

The maximum length of the inner detecting device for 18 inches subsea oil and gas pipeline is 871 mm, i.e. a magnetic detector is backward moved to the furthest position in an axial direction. When the magnetic detector is moved away from the support shaft to the furthest position in a radial direction (i.e. the inner detecting device is not entered into the pipeline yet and in a non-working state), the maximum diameter of the inner detecting device is 450 mm; when the inner detecting device is entered into the pipeline and in a working state, the maximum diameter of the magnetic detector is 428 mm; and when the magnetic detector is moved toward the support shaft to the closest position in a radial direction, the maximum diameter of the inner detecting device is 320 mm. In addition, the maximum length of the support shaft is 803 mm, the maximum diameter of the support body is 315 mm, and a total weight of the inner detecting device is 260 KG.

Figure 1:
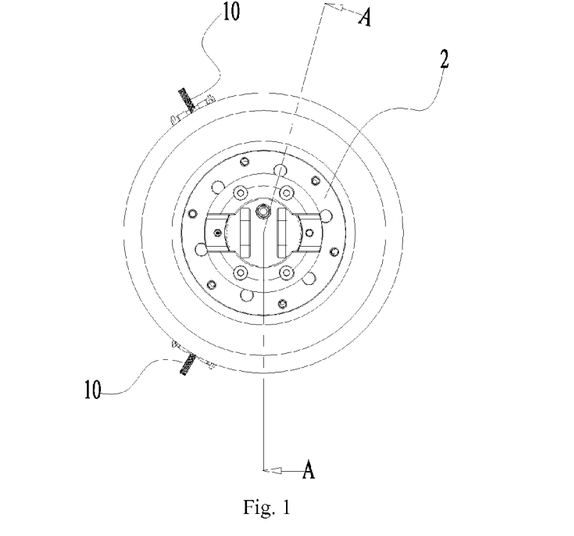
FIG. 1 is a side view of an inner detecting device for subsea oil and gas pipeline according to an embodiment of the present invention in an axial direction.
Figure 2:
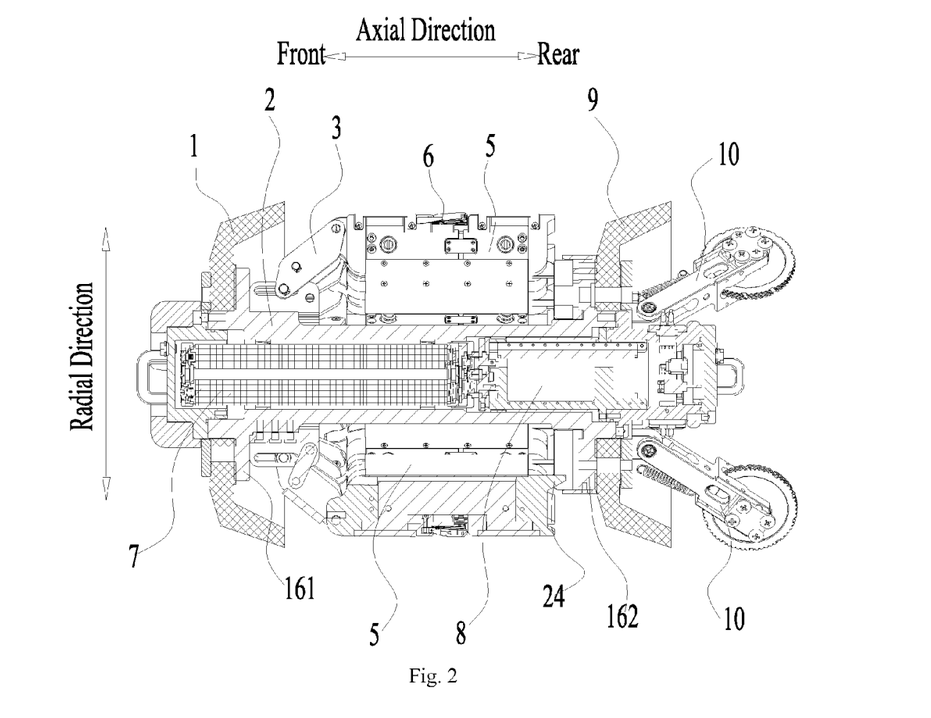
FIG. 2 is a sectional view of an inner detecting device along a A-A direction as shown in FIG. 1.

As shown in FIG. 1 and FIG. 2, the inner detecting device for the subsea oil and gas pipeline includes a support shaft 2, a packer cup, a hinge assembly 3, a magnetic detector 5, a battery pack 7, an electric recorder 8 and a mileage recorder 10.

Specifically, the support shaft 2 defines a sealed chamber therein and has a front mounting flange 161 and a rear mounting flange 162 formed along a circumferential direction of the support shaft at front and rear portions of the support shaft respectively. The packer cup may include a front packer cup 1 and a rear packer cup 9, so that the front and rear packer cups 1 and 9 are mounted to the front and rear mounting flanges 161 and 162 respectively. The front packer cup 1 and rear packer cup 9, as a drive assembly of the inner detecting device, drive the inner detecting device to move within the subsea oil and gas pipeline under acting force of the fluid within the subsea oil and gas pipeline against to the front packer cup 1 and rear packer cup 9.

The front and rear packer cups 1 and 9 have stainless press plates mounted to outsides of the front packer cup 1 and rear packer cup 9, and the stainless press plates may be fixed to the front and rear mounting flanges 161 and 162 via bolts. Moreover, a ratio of a distance between the front and rear packer cups 1 and 9 to an inner radius of the pipeline may be 1:1 to 1:1.5.

The hinge assembly 3 is coupled to the support shaft 2 and located behind the front packer cup 1, and the hinge assembly 3 is adapted to swing with respect to the support shaft 2 in a radial direction of the support shaft 2 and slide with respect to the support shaft 2 in a front-rear direction (i.e. an axial direction of the support shaft 2).

The magnetic detector 5 is parallel with the support shaft 2 and connected to the hinge assembly 3 to move with respect to the support shaft 2 in the radial and axial directions of the support shaft 2, and the magnetic detector tending to move away from the support shaft 2 in the radial direction of the support shaft. In other words, the magnetic detector 5 is normal to move away from the support shaft 2 in the radial direction, such that the magnetic detector 5 can be ensured to closely contact the inner wall of the subsea oil and gas pipeline always while the magnetic detector 5 enters into the subsea oil and gas pipeline.

The battery pack 7 and electric recorder 8 are disposed within the sealed chamber and electrically connected with each other, so that the battery pack 7 can supply power to the electric recorder 8.

The mileage recorder 10 is disposed at the rear portion of the support shaft 2 and contacts the inner wall of the pipeline, so as to record a travel distance of the inner detecting device within in the pipeline and mark the position at which a defect or leak point is detected.

Figure 3:
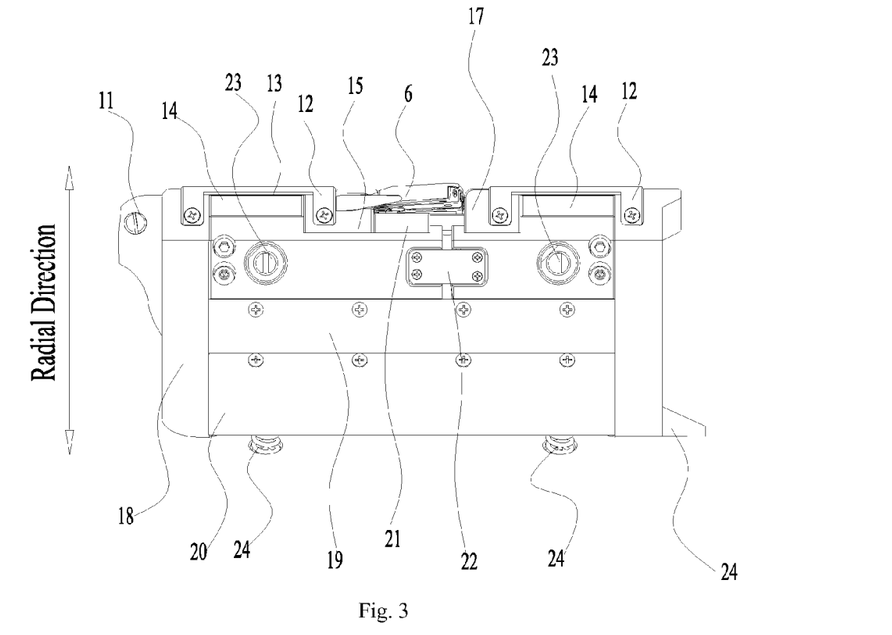
FIG. 3 is a schematic view of a magnetic detector of the inner detecting device according to an embodiment of the present invention.
Figure 5:
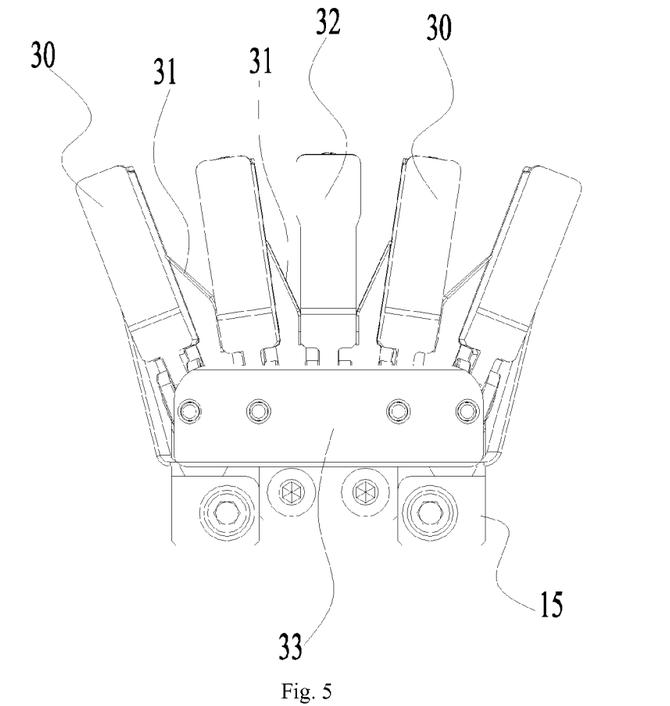
FIG. 5 is a schematic view of a finger-shaped detector of the inner detecting device according to an embodiment of the present invention.

As shown in FIG. 3 and FIG. 5, the magnetic detector 5 includes a magnetic conductor 19, a hinge mount disposed18, a plurality of magnets 14, a finger-shaped detector 6, a guide element 24 and a first elastic element 4.

The hinge mount 18 is fixed at a front end of the magnetic conductor 19 via inside hexagonal bolts and a shaft hole is formed at a front portion of the hinge mount 18 to receive a connecting shaft 11. The plurality of magnets 14 is disposed above the magnetic conductor and includes a front magnet disposed at the front portion of the magnetic conductor 19 and a rear magnet disposed a t the rear portion of the magnetic conductor 19. The front and rear magnets are respectively fixed to the magnetic conductor 19 by protecting plates 12 which are mounted to the hinge mount 18, magnetic conductor 19 and the guide element 24. A magnetic shock pad 13 may be disposed between the magnet 14 and protecting plate 12 to further protect the magnet 14. Magnetic poles of the front and rear magnets are opposite, for example, the magnetic pole of the front magnet is N pole, and the magnetic pole of the rear magnet is S pole, so as to form a closed magnetic flux loop.

Surfaces of the protecting plates 12 of for the magnets 14 may be coated with magnetic tungsten-carbide powder and treated with an anti-wear treatment. A coating thickness of the protecting plates 12 is from 0.15 to 0.25 mm. surfaces of the middle finger 32 and side fingers 30 may be coated with magnetic ceramic material and treated with an anti-wear treatment. A coating thickness of the middle finger 32 and side fingers 30 is from 0.1 to 0.2 mm.

The finger-shaped detector 6 is disposed on the magnetic conductor via a fixed seat 15 and located in a center of the closed magnetic flux loop, and a cover plate 33 is disposed above the finger-shaped detector 6. The finger-shaped detector 6 includes a middle detector 32 and a plurality of side detector 30 disposed at two sides of the middle detector 32, and a leaf spring 31 is disposed between the middle detector 32 and the side detector 30 and adjacent side detectors 30. A concentrator 21 is disposed below the finger-shaped detector 6, a block 17 for magnetic pole is located between the finger-shaped detector 6 and the rear magnet, and a wire box 20 is formed on the magnetic conductor 19.

Figure 6:
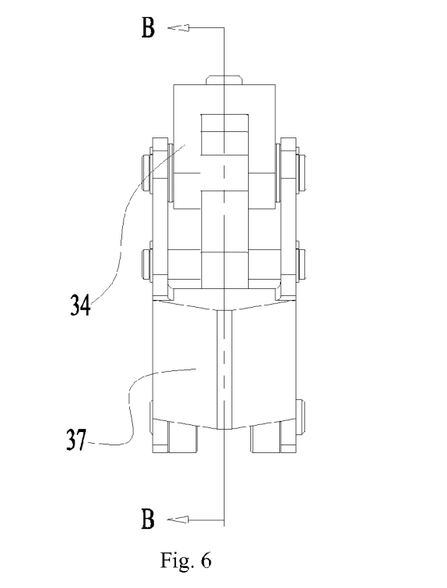
FIG. 6 is a schematic view showing cooperation between a guide element and a guide groove of the inner detecting device according to an embodiment of the present invention.
Figure 7:
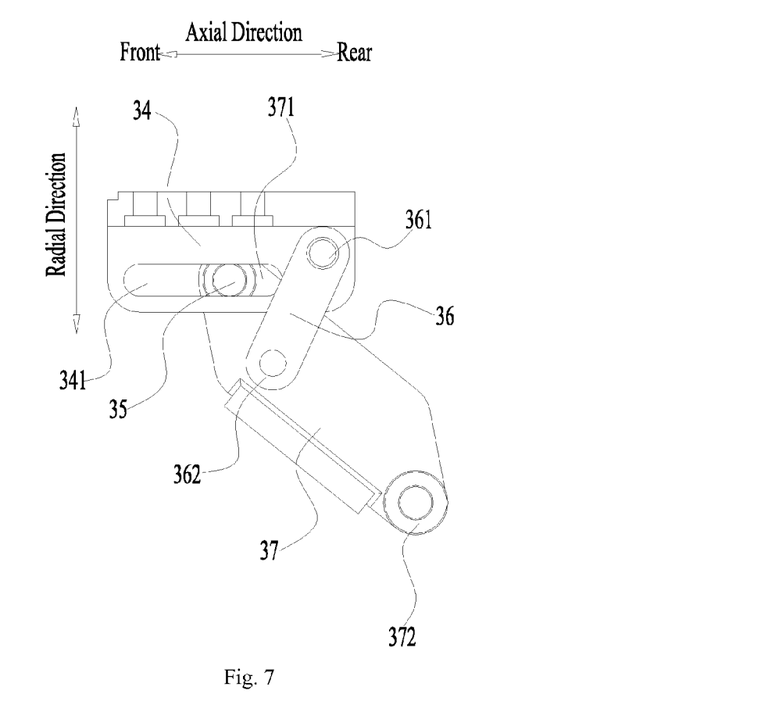
FIG. 7 is a sectional view of the guide element and guide groove as shown in FIG. 5 along a B-B direction.

At least one guide groove 38 is formed in a rear end of the support shaft 2 and extended in the radial direction of the support shaft 2, the guide element 24 is configured as a guide bar fitted into the guide groove 38 and is movable in the radial and axial directions within the guide groove 38. Due to the moving limitation of the hinge assembly 3 in the axial direction, the guide element 24 cannot go out of the guide groove 38 in the axial direction, on the other hand, due to the limitation of the walls of the guide groove 38 in the radial direction, the guide element 24 cannot go out of the guide groove 38 in radial direction.

As shown in FIG. 6 and FIG. 7, in some embodiments, one end of the guide groove is extended to an outer surface of the support shaft 2 in the radial direction, i.e. the end of the guide groove adjacent to the outer surface of the support shaft 2 is open without wall, so that the guide element 24 is easily to be fitted within the guide groove 38. A stop ring 39 is fitted over the outer surface of the support shaft 2 to prevent the guide element 24 getting from moving out of the guide groove in the radial direction.

With the structures of the guide element 24 and guide groove 38, front and rear ends of the magnetic detector 5 can obtain a certain pitch angle, so that the magnets 14 and the finger-shaped detector 6 can closely contact with the inner wall of the pipeline and the detecting accuracy of the inner detecting device of the present invention can be improved.

The number of the magnetic detectors 5 is not limited and can be adjusted according to actual need. The number of the magnetic detector 5 is equal to that of the hinge assembly 3 and preferably is at least 2.

The guide element 24 may be made of stainless steel and the surface thereof may be treated by a passivating treatment. The guide groove 38 may be made of tin bronze or manganese bronze.

The first elastic element 4 is disposed between the magnetic conductor 19 and support shaft 2 along the radial direction to normally push the magnetic conductor 19 move away from the support shaft 2 in the radial direction, i.e. the magnetic conductor 19 tends to move away from the support shaft 2 in the radial direction. Thus, the movement of the magnetic detector 5 can be dynamically adjusted according to varieties of inner diameter and shape of the inner wall of the pipeline, so as to ensure the magnetic detector 5 always closely contact with the inner wall of the pipeline.

In some embodiments, the first elastic element 4 may be configured as a spring, the magnetic conductor 19 has a mounting hole 23 and a guide post within the mounting hole 23, the spring 4 is fitted over the guide post, a first end of the spring 4 is disposed within the mounting hole and a second end of the spring 4 is contacted with the support shaft 2. A gap between the first elastic element 4 and the guide post is from 0.5 to 1 mm, and a gap between the first elastic element 4 and the mounting hole 23 is from 1 to 2 mm. Thus, the magnetic detector 5 can closely contact with the inner wall of the pipeline and is adapted to a partial deformation of the pipeline, and the trafficability of the inner detector device can be improved. Moreover, with the compressible spring 4 instead of rigid supporting between the between the magnetic conductor 19 and support shaft 2, the inner detecting device of present invention is capable of being operated in complicated structure of the pipeline.

Each of the magnetic detector 5 may have a plurality of the first elastic element 4, preferably, each of the magnetic detector 5 has two first elastic element 4 disposed at the front and rear portions of the magnetic detector 5 respectively, so that the magnetic detector 5 has sufficient and even pushing force from the first elastic elements 4.

When the magnetic detector 5 closely contacts with the inner wall of the pipeline, the closed magnetic flux loop can be formed by the inner wall of the pipeline, N pole of the front magnet, magnetic conductor 19 and S pole of the rear magnet. If there is a metal damage occurred at the wall of the subsea oil and gas pipeline, a magnetic line of the closed magnetic flux loop is twisted and deformed, then a detecting value of the magnetic detector 5 located in the center of the closed magnetic flux loop is changed, finally, the detecting value will be compared with the standard value (the detecting value without metal damage), so that the shape and size of the metal damage will be obtained.

Figure 8:
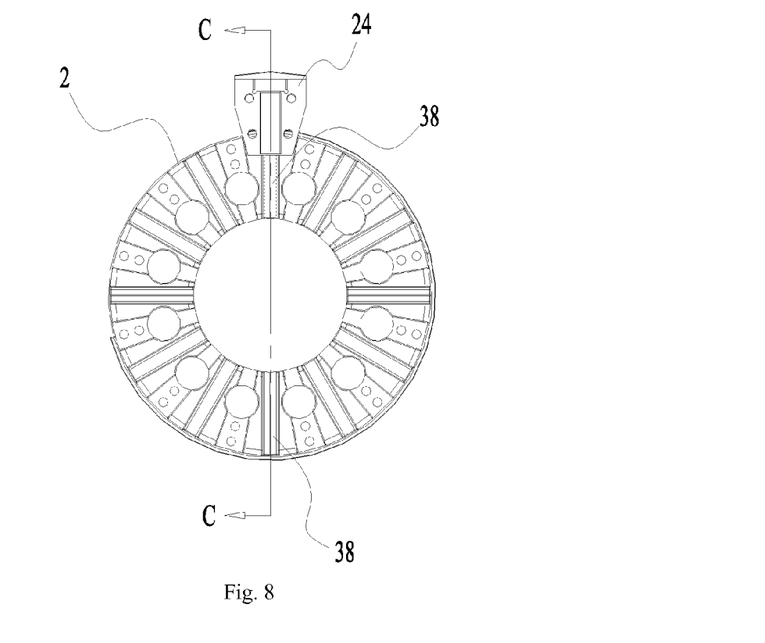
FIG. 8 is a schematic view of a hinge assembly of the inner detecting device according to an embodiment of the present invention.
Figure 9:
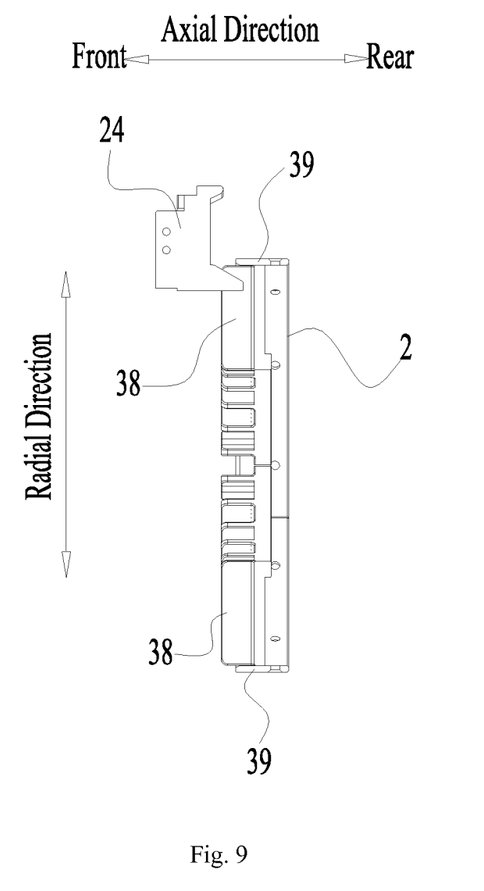
FIG. 9 is a sectional view of the hinge assembly of the inner detecting device as shown in FIG. 7 along a C-C direction.

As shown in FIG. 8 and FIG. 9, the hinge assembly 3 includes a first hinge arm 37, a second hinge arm 36 and a mounting seat 34.

The first hinge arm 37 has a first end 371 pivotally and movably coupled to the support shaft 2 and a second end 372 pivotally connected to the magnetic detector 5. The second hinge arm 36 has a first end 361 pivotally coupled to the support shaft and a second end 361 pivotally connected to the first hinge arm.

The mounting seat 34 is fixed to the support shaft 2 and defining a mounting groove 341 therein. Correspondingly, the first end 371 of the first hinge arm 37 has a pivot shaft 35 which is rotatablly and movably fitted into the mounting groove, and the first end 361 of the second hinge arm 36 is pivotally connected to the mounting seat 34.

A gap between the pivot shaft 35 and the mounting groove 341 of the mounting seat 34 may be from 0.5 to 1 mm, and the mounting seat 34 may be fixed to the support shaft 2 via a positioning flat key and a bot.

The first hinge arm 37 has a U-shaped structure, and a gap between the first hinge arm 37 and the mounting seat 34 may be from 0.5 to 1 mm. Pivot holes formed in two end of the second hinge arm 36 is clearance fit with corresponding pivot shafts, thus a gap between the pivot hole and the pivot shaft is from 0.5 to 1 mm.

With comparing this structure of two hinge arms (the first and second hinge arms 37 and 36) with a structure of a single hinge arm, the moving distance of the magnetic detector 5 in the axial direction can be reduced, thus decreasing the length of the guide element 24 and thickness of the guide groove 38. On the other hand, the distance between the front packer cup 1 and the rear packer cup 9 can be reduced, thus improving the sealing performance and reducing the power loss while the inner detecting device passing an elbow bend of the pipeline.

Figure 4:
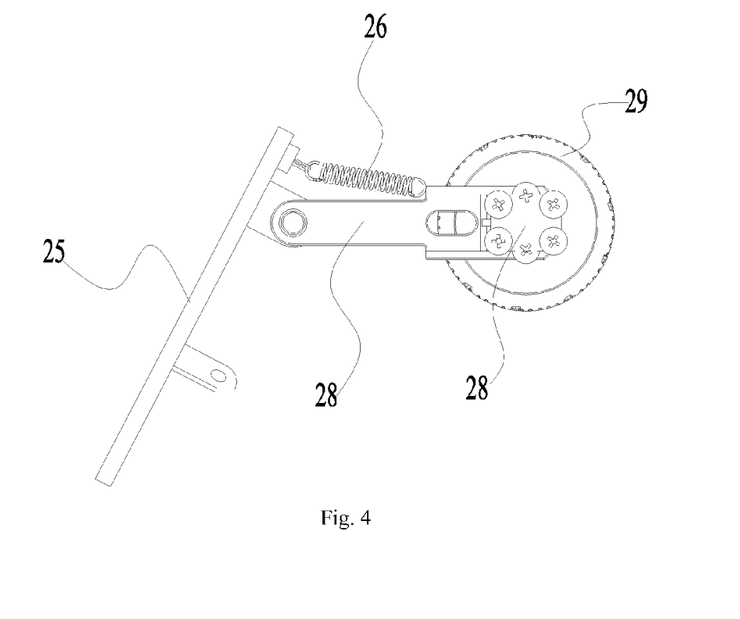
FIG. 4 is a schematic view of a mileage recorder of the inner detecting device according to an embodiment of the present invention.

As shown in FIG. 4, the mileage recorder 10 measures and records the travel distance of the inner detecting device within the pipeline, and also provides an exact position of the metal damage according to the detecting value of the magnetic detector 5. The mileage recorder 10 includes a pivot seat 25, a second elastic element 26, a swing arm 27, a rotary encoder 28 and an odometer wheel 29.

The pivot seat 25 is fixed to the support shaft 2, the swing arm 27 has a first end pivotally connected to the pivot seat 25 via a pivot shaft and a second end connected to the odometer wheel 29 which is contact with the inner wall of the subsea oil and gas pipeline and define an axis hole, and the rotary encoder 28 is disposed in the axis hole of the odometer wheel 29 to record a travel distance of the odometer wheel 29. The second elastic element 26 is connected between the swing arm 27 and the pivot seat 25 to normally pull the swing arm to rotate away from the support shaft 2, so that the odometer wheel 29 can be ensured to normally contact with the inner wall of the subsea oil and gas pipeline. Along the inner detecting device traveling within the pipeline, the odometer wheel 29 is rotated and the rotary encoder 28 records the rotation angle and the number of rotation, so as to calculate the travel distance of the inner detecting device.

The battery pack 7 includes a first radial seal, a first axial seal and a first damping element. The first radial seal is disposed between the battery pack and an inner wall of the sealed chamber in the radial direction, and the first axial seal is disposed between the battery pack and the inner wall of the sealed chamber in the axial direction. The first radial seal may be configured as an O-shaped rubber sealing ring. The first damping element is disposed on an outer surface of front and rear ends of the battery pack and made of polytetrafluoroethylene.

The electric recorder 8 includes a second radial seal, a second axial seal and a second damping element. The second radial seal is disposed between the electric recorder and an inner wall of the sealed chamber in the radial direction, the second axial seal is disposed between the electric recorder and the inner wall of the sealed chamber in the axial direction. The second radial seal may be configured as an O-shaped rubber sealing ring. The second damping element is disposed on an outer surface of front and rear ends of the electric recorder 8 and made of polytetrafluoroethylene.

The battery pack 7 and the electric recorder 8 are coaxially disposed and the rear end of the battery pack 7 is connected to the front end of the electric recorder 8.

The rear mounting flange 162 defines a through-hole therein, a plurality of wires of the finger-shaped detector 6 are concentrated to be a wire harness via the concentrator 21, then a plug of the wire harness is connected to a socket of the electric recorder 8 through the through hole, so that the finger-shaped detector 6 is electrically connected to the electric recorder 8. A quick-drying silicone rubber is filled within the through-hole to eliminate a gap between the wire harness and the through-hole, so as to ensure the sealing performance of the rear packer cup 9.

The plug and the socket are made of nitrile-butadiene rubber and capable of bearing pressure of 0-20 MPa.

A working principle of the inner detecting device of the present invention it that when the magnetic detector 5 closely contacts with the inner wall of the subsea oil and gas pipeline, the closed magnetic flux loop can be formed by the inner wall of the pipeline, N pole of the front magnet, magnetic conductor 19 and S pole of the rear magnet. If there is a metal damage occurred at the wall of the subsea oil and gas pipeline, a magnetic line of the closed magnetic flux loop is twisted and deformed, then a detecting value of the magnetic detector 5 located in the center of the closed magnetic flux loop is changed, finally, the detecting value will be compared with the standard value (the detecting value without metal damage), so that the shape and size of the metal damage will be obtained.

The wires of the finger-shaped detector 6 are concentrated to be a wire harness via the concentrator 21, and then a plug of the wire harness is connected to a socket of the electric recorder 8 via the through hole, so that the finger-shaped detector 6 is electrically connected to the electric recorder 8 and detecting and recording c circuits are formed.

Along the inner detecting device traveling within the pipeline due to the driving force from the fluid within the pipeline applied to the front packer cup 1 and rear packer cup 9, the odometer wheel 29 is rotated and the rotary encoder 28 records the rotation angle and the rotation number of the odometer wheel 29, so as to calculate the travel distance of the inner detecting device.

Thus, the metal damage and the exact position of the metal damage can be detected by the inner detecting device according to embodiments of the present invention.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present invention. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present invention. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present invention, and changes, alternatives, and modifications can be made in the embodiments without departing from spirit, principles and scope of the present invention.

What is claimed is:

1. An inner detecting device for subsea oil and gas pipeline, comprising:
   a support shaft defining a sealed chamber therein;
   a packer cup coupled to the support shaft along a circumferential direction of the support shaft
   a hinge assembly coupled to the support shaft, swinging with respect to the support shaft in a radial direction of the support shaft and sliding with respect to the support shaft in an axial direction of the support shaft;
   a magnetic detector connected to the hinge assembly to move with respect to the support shaft in the radial and axial directions of the support shaft, and the magnetic detector tending to move away from the support shaft in the radial direction of the support shaft;
   a battery pack disposed within the sealed chamber;
   an electric recorder disposed within the sealed chamber and electrically connected to the battery pack; and
   a mileage recorder disposed on the support shaft to record a travel distance of the inner detecting device within the pipeline,
   wherein the hinge assembly comprises: a first hinge arm having a first end pivotally and movably coupled to the support shaft and a second end pivotally connected to the magnetic detector; and a second hinge arm having a first end pivotally coupled to the support shaft and a second end pivotally connected to the first hinge arm,
   wherein the magnetic detector comprises:
   a magnetic conductor;
   a hinge mount disposed at a front end of the magnetic conductor and pivotally connected to the second end of the first hinge arm via a connecting shaft;
   a plurality of magnets disposed above the magnetic conductor to form a closed magnetic flux loop;
   a finger-shaped detector disposed on the magnetic conductor and located in a center of the closed magnetic flux loop;
   a guide element disposed at rear end of the magnetic conductor and coupled to the support shaft, and the guide element being moved with respect to the support shaft in the radial and axial directions of the support shaft; and
   a first elastic element disposed between the magnetic conductor and support shaft to normally push the magnetic conductor move away from the support shaft in the radial direction of the support shaft.

2. The inner detecting device of claim 1, wherein the first elastic element is a spring, the magnetic conductor has a mounting hole and a guide post within the mounting hole, the spring is fitted over the guide post, a first end of the spring is disposed within the mounting hole and a second end of the spring is contacted with the support shaft.

3. The inner detecting device of claim 1, wherein a number of the magnetic detector is equal to that of the hinge assembly and is at least 2.

4. The inner detecting device of claim 1, wherein the mileage recorder comprises:
   a pivot seat fixed to the support shaft;
   a swing arm having a first end pivotally connected to the pivot seat via a pivot shaft and a second end;
   an odometer wheel connected to the second end of the swing arm to contact with an inner wall of the subsea oil and gas pipeline and defining an axis hole;
   a rotary encoder disposed in the axis hole of the odometer wheel to record a travel distance of the odometer wheel; and
   a second elastic element connected between the swing arm and the pivot seat to normally drive the swing arm to rotate away from the support shaft.

5. The inner detecting device of claim 1, wherein the hinge assembly further comprises a mounting seat fixed to the support shaft and defining a mounting groove therein, the first end of the first hinge arm has a pivot shaft rotatably and movably fitted into the mounting groove, and the first end of the second hinge arm is pivotally connected to the mounting seat.

6. The inner detecting device of claim 1, wherein the support shaft define a guide groove formed in a rear end of the support shaft and extended in the radial direction of the support shaft, the guide element is fitted into the guide groove and is movable in the radial and axial directions of the support shaft within the guide groove.

7. The inner detecting device of claim 6, wherein one end of the guide groove is extended to an outer surface of the support shaft in the radial direction of the support shaft, and a stop ring is fitted over the outer surface of the support shaft to prevent the guide element getting from moving out of the guide groove in the radial direction of the support shaft.

8. The inner detecting device of claim 1, wherein the packer cup comprises front and rear packer cups, and a ratio of a distance between the front and rear packer cups to an inner radius of the pipeline is 1:1 to 1:1.5.

9. The inner detecting device of claim 8, wherein front and rear mounting flanges are formed at front and rear portions of the support shaft respectively, and the front and rear packer cups are mounted to the front and rear mounting flanges respectively via stainless press plates.

10. An inner detecting device for subsea oil and gas pipeline, comprising:
a support shaft defining a sealed chamber therein;
a packer cup coupled to the support shaft along a circumferential direction of the support shaft
a hinge assembly coupled to the support shaft, swinging with respect to the support shaft in a radial direction of the support shaft and sliding with respect to the support shaft in an axial direction of the support shaft;
a magnetic detector connected to the hinge assembly to move with respect to the support shaft in the radial and axial directions of the support shaft, and the magnetic detector tending to move away from the support shaft in the radial direction of the support shaft;
a battery pack disposed within the sealed chamber;
an electric recorder disposed within the sealed chamber and electrically connected to the battery pack; and
a mileage recorder disposed on the support shaft to record a travel distance of the inner detecting device within the pipeline,
wherein the packer cup comprises front and rear packer cups, and a ratio of a distance between the front and rear packer cups to an inner radius of the pipeline is 1:1 to 1:1.5,
wherein front and rear mounting flanges are formed at front and rear portions of the support shaft respectively, and the front and rear packer cups are mounted to the front and rear mounting flanges respectively via stainless press plates, wherein the magnetic detector further comprises a concentrator disposed below the finger-shaped detector, the rear mounting flange defines a through-hole therein, a plurality of wires of the finger-shaped detector are concentrated to be a wire harness via the concentrator, so that a plug of the wire harness is connected to a socket of the finger-shaped detector through the through hole, the plug and the socket are made of nitrile-butadiene rubber and capable of bearing pressure of 0-20 MPa.

11. An inner detecting device for subsea oil and gas pipeline, comprising:
a support shaft defining a sealed chamber therein;
a packer cup coupled to the support shaft along a circumferential direction of the support shaft;
a hinge assembly coupled to the support shaft, swinging with respect to the support shaft in a radial direction of the support shaft and sliding with respect to the support shaft in an axial direction of the support shaft;
a magnetic detector connected to the hinge assembly to move with respect to the support shaft in the radial and axial directions of the support shaft, and the magnetic detector tending to move away from the support shaft in the radial direction of the support shaft;
a battery pack disposed within the sealed chamber;
an electric recorder disposed within the sealed chamber and electrically connected to the battery pack; and
a mileage recorder disposed on the support shaft to record a travel distance of the inner detecting device within the pipeline,
wherein the battery pack comprises:
a first radial seal disposed between the battery pack and an inner wall of the sealed chamber in the radial direction of the support shaft,
a first axial seal disposed between the battery pack and the inner wall of the sealed chamber in the axial direction of the support shaft; and
a first damping element disposed on an outer surface of the battery pack and made of polytetrafluoroethylene.

12. The inner detecting device of claim 11, wherein the electric recorder comprises:
a second radial seal disposed between the electric recorder and an inner wall of the sealed chamber in the radial direction of the support shaft,
a second axial seal disposed between the electric recorder and the inner wall of the sealed chamber in the axial direction of the support shaft; and
a second damping element disposed on an outer surface of the electric recorder and made of polytetrafluoroethylene.

13. The inner detecting device of claim 11, wherein the battery pack and the electric recorder are coaxially disposed and a rear end of the battery pack is connected to a front end of the electric recorder.

* * * * *